US011814347B2

(12) United States Patent
Friedrich et al.

(10) Patent No.: US 11,814,347 B2
(45) Date of Patent: Nov. 14, 2023

(54) METHOD FOR PRODUCING FLUORINATED COMPOUNDS

(71) Applicant: MERCK PATENT GMBH, Darmstadt (DE)

(72) Inventors: Reiner Friedrich, Seeheim-Jugenheim (DE); Fabian Koch, Pfungstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 17/553,256

(22) Filed: Dec. 16, 2021

(65) Prior Publication Data

US 2022/0106245 A1 Apr. 7, 2022

Related U.S. Application Data

(62) Division of application No. 16/649,805, filed as application No. PCT/EP2018/075725 on Sep. 24, 2018, now Pat. No. 11,247,960.

(30) Foreign Application Priority Data

Sep. 26, 2017 (EP) ..................... 17193044

(51) Int. Cl.
| | |
|---|---|
| C07C 43/13 | (2006.01) |
| C07C 41/14 | (2006.01) |
| C07C 41/03 | (2006.01) |
| C07C 17/263 | (2006.01) |
| C07C 17/272 | (2006.01) |
| C09D 5/00 | (2006.01) |
| C09D 7/61 | (2018.01) |
| C09D 7/40 | (2018.01) |
| C07D 303/24 | (2006.01) |

(52) U.S. Cl.
CPC .......... *C07C 41/14* (2013.01); *C07C 17/2637* (2013.01); *C07C 17/272* (2013.01); *C07C 41/03* (2013.01); *C07C 43/137* (2013.01); *C07D 303/24* (2013.01); *C09D 5/006* (2013.01); *C09D 7/40* (2018.01); *C09D 7/61* (2018.01)

(58) Field of Classification Search
None
See application file for complete search history.

(56) References Cited

U.S. PATENT DOCUMENTS

| | | |
|---|---|---|
| 5,608,116 A | 3/1997 | Halling et al. |
| 10,464,874 B2 | 11/2019 | Friedrich et al. |
| 2017/0349760 A1 | 12/2017 | Friedrich |

FOREIGN PATENT DOCUMENTS

| | | | |
|---|---|---|---|
| WO | 15124290 A1 | 8/2015 | |
| WO | WO-2015124290 A1 * | 8/2015 | ........... C07C 217/28 |
| WO | 16096129 A1 | 6/2016 | |

OTHER PUBLICATIONS

Wo2015124290a1, machine translation, Aug. 2015, pp. 1-44 (Year: 2015).*
D. Solov'ev et al., Fluorine-containing 2,3, Epoxypropyl Ethers . . . The Journal of General Chemistry of the USSR (Engl. Transl.), vol. 61, 1991, 611-615, XP009509481.
International Search Report PCT/2018EP/ 075725 dated Nov. 27, 2018 pp. 1-2.
Sigma (1-octanol, Deposit and Available date Mar. 3, 2017 (Year: 2017).
Zinc (Perfluoropropanol, Deposit and Available date Dec. 10, 2015) (Year: 2015).
Bazhin, D. N. et al. "Features of Reaction between Fluorine-Containing Glycidyl Ethers and Alcohols in Basic Medium" Russian Journal of Organic Chemistry, 2007, vol. 43, No. 5, pp. 656-659 (Year: 2007).
Solov'ev, D. V. et al. "Fluorine-containing glycidyl ethers. Synthesis and spectra" Zhumal Obshchei Khimii, 1991, vol. 61, 673-678 (Year: 1991).
Kang, E-k. et al. "Synthesis and surface active properties of novel anionic surfactants with two short fluoroalkyl groups" Journal of Industrial and Engineering Chemistry 61 (2018) 216-226; available online Dec. 20, 2017 (Year: 2017).

* cited by examiner

*Primary Examiner* — Medhanit W Bahta
(74) *Attorney, Agent, or Firm* — MILLEN WHITE ZELANO AND BRANIGAN, PC; Csaba Henter

(57) ABSTRACT

The present invention relates to a process for the preparation of fluorinated compounds, to novel compounds containing fluorinated end groups, to the use thereof and to compositions comprising novel compounds containing fluorinated end groups.

16 Claims, No Drawings

METHOD FOR PRODUCING FLUORINATED COMPOUNDS

The present invention relates to a process for the preparation of fluorinated compounds, to novel compounds containing fluorinated end groups, to the use thereof, and to compositions comprising novel compounds containing fluorinated end groups.

Fluorine compounds are an important constituent in industrial process chemicals. Fluorine-containing compounds can be employed in a very wide variety of applications and contribute, for example, to improved wetting of surfaces. Thus, they are used, for example, as interface promoter or emulsifier or viscosity reducer in paints, coatings or adhesives or in dirt-repellent coatings, for example in the textile industry.

Classical fluorine compounds are built up from long-chain, perfluorinated alkyl chains (C6-C8) and are regarded as potentially bioaccumulative and toxic. Owing to their persistence and toxicity, these materials are problematic for users and the environment.

Shorter-chain fluorine building blocks are more favourable from their ecotoxicological profiles, but often exhibit poorer properties in their areas of application.

Branched fluorosurfactants have also been known for some time. Owing to the synthetic processes to date, the fluorine chains in branched fluorine compounds always have the same chain length. There is therefore a need for novel fluorine-containing compounds and for processes for the preparation of compounds which contain different fluorine-containing groups.

The present invention relates to a process for the preparation of fluorinated compounds of formula (I)

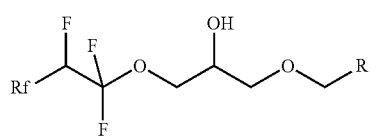

(I)

where firstly comounds of formula (II)

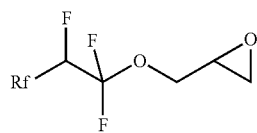

(II)

are prepared and these are then converted into the compouns of the formula (I) in a manner known per se, wherein
Rf is a fluorinated, linear or branched alkyl group, optionally containing further heteroatoms,
R is a linear or branched alkyl or siloxane group, optionally containing heteroatoms, or a group Rf', and
Rf' is a fluorinated, linear or branched alkyl group, optionally containing further heteroatoms,
to fluorinate compounds of the formulae (I'), (II) and (VI'), to uses thereof, and to compositions containing a compound of formula (VI') and a vehicle which is suitable for the respective application and optionally further specific active substances.

The present invention now makes it possible to prepare not only branched fluorinated compounds containing identical fluorinated end groups, but also branched fluorine compounds and fluorine-containing, functionalisable compounds having an asymmetrical structure.

The process according to claim 1 according to the invention enables the preparation of branched, fluorine-containing compounds of the formula (I) which contain different fluorine-containing groups, for example fluorine-containing alkyl chains having different chain lengths, starting from known, commercially available compounds. The novel process is also suitable for the preparation of "mixed-branched" compounds, i.e. compounds which contain both fluorine-containing and fluorine-free groups. The process can equally also be utilised for the preparation of branched compounds containing identical fluorine-containing groups.

The branched alcohols of the formula (I) can then be converted into the corresponding fluorinated surfactants, for example anionic or non-ionic surfactants, or fluorinated acrylates or silanes.

The preparation of fluorinated materials having chains of different lengths has a number of advantages. Thus, the properties with respect to CMC and surface-tension reduction can be manipulated in a further environment than is possible in the case of chains of equal length.

In solvent-containing paint systems, the combination of fluorinated and unfluorinated hydrocarbon surfactants is often recommended. The combination of fluorinated and unfluorinated chains in one molecule thus gives rise to the expectation of synergies that are not possible on use of pure fluorosurfactants.

The present invention relates firstly to a process according to claim 1 for the preparation of fluorinated compounds of the formula (I)

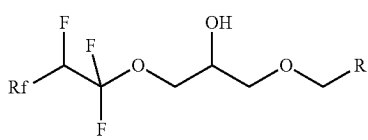

(I)

where
Rf is a fluorinated, linear or branched alkyl group, optionally containing further heteroatoms,
R is a linear or branched alkyl or siloxane group, optionally containing heteroatoms, or a group Rf', and
Rf' is a fluorinated, linear or branched alkyl group, optionally containing further heteroatoms.

In a first step of the process, a compound of the formula (II), in which Rf is a fluorinated, linear or branched alkyl group, optionally containing further heteroatoms, is prepared

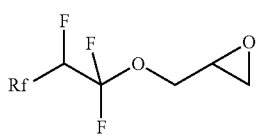

(II)

and this is then converted into compounds of the formula (I) in a manner known per se.

The process according to the invention preferably comprises the following steps, where Rf, R and Rf' have the meanings given for the formulae (I) and (II):

a) reaction of compounds of the formula (III) with glycidol (IV) to give compounds of the formula (II)

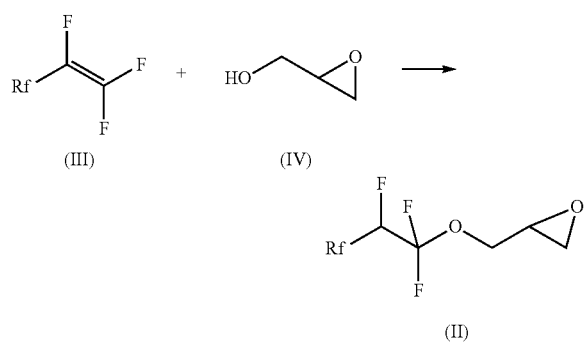

and
b) reaction of compounds of the formula (II) with alcohols of the formula (V) to give compounds of the formula (I)

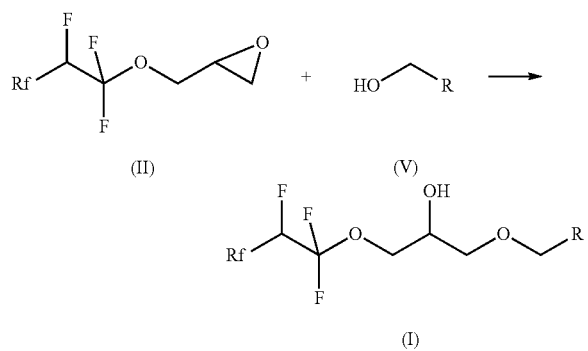

Rf is preferably a group of the formula

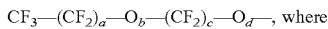
$CF_3$—$(CF_2)_a$—$O_b$—$(CF_2)_c$—$O_d$—, where a=0, 1, 2 or 3,
b=0 or 1,
c=0, 1, 2 or 3 and
d=0 or 1.
Rf' is preferably a group of the formula

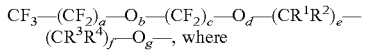
$CF_3$—$(CF_2)_a$—$O_b$—$(CF_2)_c$—$O_d$—$(CR^1R^2)_e$—$(CR^3R^4)_f$—$O_g$—, where $R^1$, $R^2$, $R^3$ and $R^4$, independently of one another, are hydrogen or an alkyl group,
a=0, 1, 2 or 3,
b=0 or 1,
c=0, 1, 2 or 3,
d=0 or 1,
e=0, 1, 2, 3 or 4,
f=0, 1, 2, 3 or 4 and
g=0 or 1.

The groups Rf and/or Rf' can preferably be a fluorinated C1-C6-alkyl group, particularly preferably a perfluorinated C1-C4-alkyl group, in particular a perfluorinated C3-alkyl group.

The groups Rf and Rf' are preferably not identical.

In a variant of the process, however, the groups Rf and Rf' may also be identical.

On use of siloxane-containing alcohols, the use of 1-propanol, 3-[1,3,3,3 tetramethyl-1-[(trimethylsilypoxy]-1-disiloxanyl]- (Va) is particularly suitable since this compound is commercially available and is employed in numerous surfactant applications.

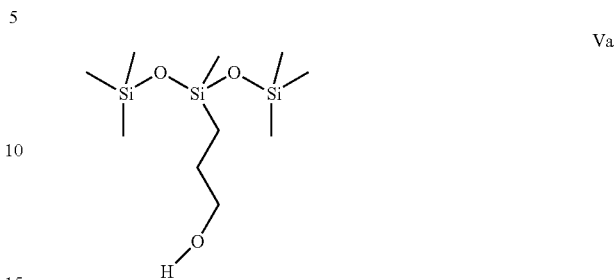

Process steps a) and b) according to the invention are preferably carried out as follows:

The conversion to formula (II) here is preferably carried out in an inert solvent (preferably an ether, for example dioxane or THF), a base (in particular carbonates or hydroxides of the alkali metals or alkaline-earth metals, preferably $K_2CO_3$ or NaOH), the corresponding fluoroolefin and glycidol.

Glycidol is preferably employed here in a stoichiometric or slightly sub-stoichiometric (1:1-1:0.85) ratio to the fluoroolefin. The latter simplifies work-up and improves the yields. This reaction mixture is brought to reaction in a pressure reactor, in particular at 80-140° C., preferably 110° C., until the pressure drop flattens out (generally 12-24 h). The work-up is carried out by washing by shaking with water and drying of the organic phase. The yields are between 60-95%, based on the glycidol. The partially fluorinated oxides can be purified well by distillation under reduced pressure.

For the further reaction, epoxides and the corresponding alcohols are brought to reaction with a catalyst system. Use is preferably made here of a mixture of $NaBH_4$, NaI and 12 as described under U.S. Pat. No. 5,608,116.

Alternatively, the reaction can be carried out with elemental Na or boron tri-fluoride diethyl ether. To this end, the alcohol is initially introduced, the reagent is added under inert conditions and with cooling, and the epoxide is slowly metered in. When the addition is complete, the batch is slowly warmed to 80° C. and stirred vigorously for several hours. Suitable alcohols for the additive ring opening here, besides fluorinated C1-C6-alcohols, are also purely aliphatic alcohols or ether alcohols having a total chain length of C1-C20, preferably C6-C14. However, other H-acidic compounds, such as, for example, siloxanes or thiols, are also possible.

The invention also relates to the intermediates of the process, i.e. the compounds of the formula (II), where Rf is a fluorinated, linear or branched alkyl group, optionally containing further heteroatoms, according to claim 7:

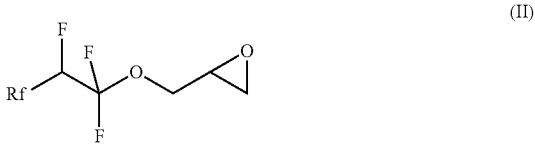

Rf is preferably a group of the formula $CF_3$—$(CF_2)_a$—$O_b$—$(CF_2)_c$—$O_d$—,
where a=0, 1, 2 or 3, b=0 or 1, c=0, 1, 2 or 3 and d=0 or 1.

Rf is particularly preferably a group of the formula

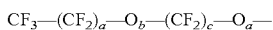

where a=1 or 2, b=1, c=0 and d=0.

The present invention also relates to compounds of the formula (I') according to claim 9.

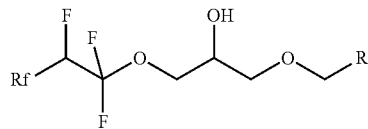

where
Rf is a fluorinated, linear or branched alkyl group, optionally containing further heteroatoms,
R is a linear or branched alkyl or siloxane group, optionally containing heteroatoms, or a group Rf',
Rf' is a fluorinated, linear or branched alkyl group, optionally containing further heteroatoms,
and, if R is a group Rf', Rf and Rf' are different.

Preference is given to compounds of the formula (I') in which Rf is a group of the formula $CF_3$—$(CF_2)_{0-3}$— or $CF_3$—$(CF_2)_{0-3}$—O—.

Rf is particularly preferably a group of the formula

where a=1 or 2, b=1, c=0 and d=0.

The group R can preferably be a C1-C20 alkyl group, in particular a C6-C14 alkyl group, or a siloxane group.

Rf' is preferably a group of the formula

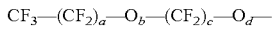

where
$R^1$, $R^2$, $R^3$ and $R^4$, independently of one another, are hydrogen or an alkyl group,
a=0, 1, 2 or 3,
b=0 or 1, in particular 1
c=0, 1, 2 or 3, in particular 0
d=0 or 1, in particular 0
e=0, 1, 2, 3 or 4, in particular 0 and 1
f=0, 1, 2, 3 or 4, in particular 0, and
g=0 or 1, in particular 0.

Particular preference is given to compounds of the formula (I') in which Rf and Rf' have the preferred meanings.

R is furthermore preferably $CH_2$—$CH_2$—Si $(CH_3)[O$—$Si(CH_3)_3]_2$

The invention furthermore relates to the use of compounds of the formula (I) for the preparation of compounds of the formula (VI):

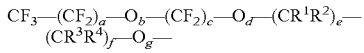

where
Rf is a fluorinated, linear or branched alkyl group, optionally containing further heteroatoms,
R is a linear or branched alkyl or siloxane group, optionally containing heteroatoms, or a group Rf',
Rf' is a fluorinated, linear or branched alkyl group, optionally containing further heteroatoms,
L is a single bond or a divalent organic group and
X is a cationic, non-ionic, amphoteric or anionic group.

The groups Rf, R, and Rf' preferably have the meanings given for the formula (I), in particular the preferred meanings.

The introduction of the hydrophilic, anionic, cationic, reactive or polymerisable end group is possible for the person skilled in the art by known methods.

An example of non-ionic surfactants which should be mentioned here would be polyethylene glycol or polypropylene glycol or copolymers thereof, which can be prepared from the corresponding monomeric epoxides. It is advantageous in the case of these compounds that the so-called HLB value of the compound can be set via the chain length.

Reaction of the alcohol with glycidyltrimethylammonium chloride gives cationic surfactants.

A simple method for the preparation of anionic surfactants is the preparation of so-called phosphoric acid esters. In this method, the fluorinated alcohol is reacted with $P_2O_5$ or $POCl_3$ and neutralised using a base. A further possibility for the preparation of anionic surfactants is reaction of the alcohol with $SO_3$ or concentrated sulfuric acid to give so-called sulfates.

Polymerisable groups which may be mentioned in particular are the (meth)-acrylates, which can be obtained from the corresponding acid chlorides or anhydrides.

The invention furthermore also relates to the corresponding fluorinated surfactants and fluorinated compounds containing anchor groups, for example fluorinated acrylates, which can be prepared from the branched alcohols of the formula (I'). These compounds are represented by the formula (VI'), where X stands for a hydrophilic group, preferably an anionic, cationic, non-ionic group or an anchor group, preferably an ethylenically unsaturated group, in particular an acrylate or methacrylate group, an alkoxysilane group or a halosilane group, and L is a single bond or a divalent organic group.

The present invention thus relates to compounds of the formula (VI') according to claim 14:

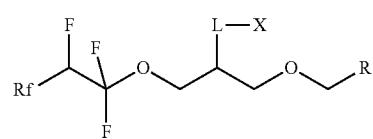

where
Rf is a fluorinated, linear or branched alkyl group, optionally containing further heteroatoms,
R is a linear or branched alkyl group, optionally containing heteroatoms, or a group Rf',
Rf' is a fluorinated, linear or branched alkyl group, optionally containing further heteroatoms,
L is a single bond or a divalent organic group and
X is a cationic, non-ionic, amphoteric or anionic group
and, if R is a group Rf', Rf and Rf' are different.

The compounds of the formula (VI') preferably contain a group Rf having the formula $CF_3$—$(CF_2)_{0-3}$— or $CF_3$—$(CF_2)_{0-3}$—O—.

The group R can preferably be a C1-C20 alkyl group, in particular a C6-C14 alkyl group.

Rf' is preferably a group of the formula $$CF_3-(CF_2)_a-O_b-(CF_2)_c-O_d-(CR^1R^2)_e-(CR^3R^4)_f-O_g-$$

where
R$^1$, R$^2$, R$^3$ and R$^4$, independently of one another, are hydrogen or an alkyl group,
a=0, 1, 2 or 3
b=0 or 1, in particular 1
c=0, 1, 2 or 3, in particular 0
d=0 or 1, in particular 0
e=0, 1, 2, 3 or 4, in particular 0 and 1
f=0, 1, 2, 3 or 4, in particular 0, and
g=0 or 1, in particular 0.

Particular preference is given to compounds of the formula (VI') in which Rf and Rf' have the preferred meanings.

A preferred anionic group X can be selected from —COO$^-$, —SO$_3^-$, —OSO$_3^-$, —PO$_3^{2-}$, —OPO$_3^{2-}$, —(OCH$_2$CH$_2$)$_s$—O—(CH$_2$)$_t$—COO$^-$, —(OCH$_2$CH$_2$)$_s$—O—(CH$_2$)$_t$—SO$_3^-$, —(OCH$_2$CH$_2$)$_s$—O—(CH$_2$)$_t$—OSO$_3^-$, —(OCH$_2$CH$_2$)$_s$—O—(CH$_2$)$_t$—PO$_3^{2-}$, —(OCH$_2$CH$_2$)$_s$—O—(CH$_2$)$_t$—OPO$_3^{2-}$
where s stands for an integer from the range from 1 to 1000 and t stands for an integer selected from 1, 2, 3 or 4.

The preferred anionic groups here include, in particular, —COO$^-$, —SO$_3^-$, —OSO$_3^-$, —PO$_3^{2-}$, —OPO$_3^{2-}$, the subformula A, and —(OCH$_2$CH$_2$)$_s$—O—(CH$_2$)$_t$—COO$^-$, —(OCH$_2$CH$_2$)$_s$—O—(CH$_2$)$_t$—SO$_3^-$ and —(OCH$_2$CH$_2$)$_s$—O—(CH$_2$)$_t$—OSO$_3^-$, where each one of these groups per se may be preferred. X can also stand for the corresponding acids.

The very particularly preferred anionic groups here include —SO$_3^-$, —OSO$_3^-$, —COO$^-$, —PO$_3^{2-}$, or OPO$_3^{2-}$. In particular, a sulfonate group —SO$_3^-$ is preferred. Preferred counterion for anionic groups X is a monovalent cation, in particular H$^+$, an alkali-metal cation or NR$_4^+$, where R=H or C1-C6-alkyl and all R may be identical or different. Especial preference is given to H$^+$, Na$^+$, K$^+$, Li$^+$ and NH$_4^+$, particularly preferably Na$^+$.

A preferred cationic group X can be selected from —NR$^1$R$^2$R$^3$+Z$^-$, —PR$^1$R$^2$R$^3$+Z$^-$, where R stands for H or C1-4-alkyl in any desired position,
Z$^-$ stands for Cl$^-$, Br$^-$, I$^-$, CH$_3$SO$_3^-$, CF$_3$SO$_3^-$, CH$_3$PhSO$_3^-$, PhSO$_3^-$
R$^1$, R$^2$ and R$^3$ each, independently of one another, stand for H, C$_{1-30}$-alkyl, Ar or CH$_2$Ar and
Ar stands for an unsubstituted or mono- or polysubstituted aromatic ring or condensed ring systems having 6 to 18 C atoms, in which, in addition, one or two CH groups may be replaced by N.

The preferred cationic groups here include, in particular, —NR$^1$R$^2$R$^3$+Z$^-$ and where each one of these groups per se may be preferred.

A preferred non-ionic group can be selected from: linear or branched alkyl, where one or more non-adjacent C atoms have been replaced by O, S, and/or N, —OH, —SH, —O-(glycoside)$_{o'}$, —S-(glycoside)$_{o'}$, —OCH$_2$—CHOH—CH$_2$—OH, —O CH$_2$Ar(—NCO)$_{p'}$, —OAr(—NCO)$_{p'}$, amine oxide, u stands for an integer from the range from 1 to 6, preferably 1 to 4
o' stands for an integer from the range from 1 to 10,
p' stands for 1 or 2,
Ar stands for an unsubstituted, mono- or polysubstituted aromatic ring or condensed ring systems having 6 to 18 C atoms, in which, in addition, one or two CH groups may be replaced by C=O and,
glycoside stands for an etherified carbohydrate, preferably for a mono-, di-, tri- or oligoglucoside.

The preferred non-ionic groups X here include, in particular, linear or branched alkyl, where one or more non-adjacent C atoms have been replaced by O, S and/or N, —OH and —O-(glycoside)$_{o'}$.

If X=alkyl, where one or more non-adjacent C atoms have been replaced by O, S, and/or N, it is then preferably equal to R$^4$-(B-A)$_{m''}$-, where R$^4$=H or C1-4-alkyl, in particular H or CH$_3$, A=linear or branched alkylene, preferably having 1 to 10 carbon atoms, in particular having 1 to 4 carbon atoms, B=O or S, preferably O, and m''=an integer preferably from the range from 1 to 100, particularly preferably 1 to 30.

The non-ionic group X is particularly preferably the group R$^4$—(O—CH$_2$CHR$^5$)$_{m''}$-, where m''=an integer from the range from 1 to 100, preferably 1 to 30, in particular also 1-25, and R$^4$ and R$^5$=H or C1-4-alkyl, in particular H or CH$_3$. R$^4$—(B-A)$_{m''}$ is particularly preferably a polyethylene glycol or polypropylene glycol unit.

The non-ionic group X is particularly preferably the group —CH(OH)—CH$_2$—NH-sach, where sach=various sugars and the group —Y—(CH$_2$—CH$_2$—O)$_v$—R$^4$ where Y=S, O or NH, preferably O, R$^4$=H or alkyl, preferably H or CH$_3$, and v=1-100, preferably 1-30, in particular also 1-25.

A preferred amphoteric group X can be selected from the functional groups of the acetyldiamines, the N-alkylamino acids, the N-alkylaminosulfonic acids, the betaines, the sulfobetaines, or corresponding derivatives, in particular selected from the following groups, where M stands for H or an alkali-metal ion, preferably Li$^+$, Na$^+$ or K$^+$:

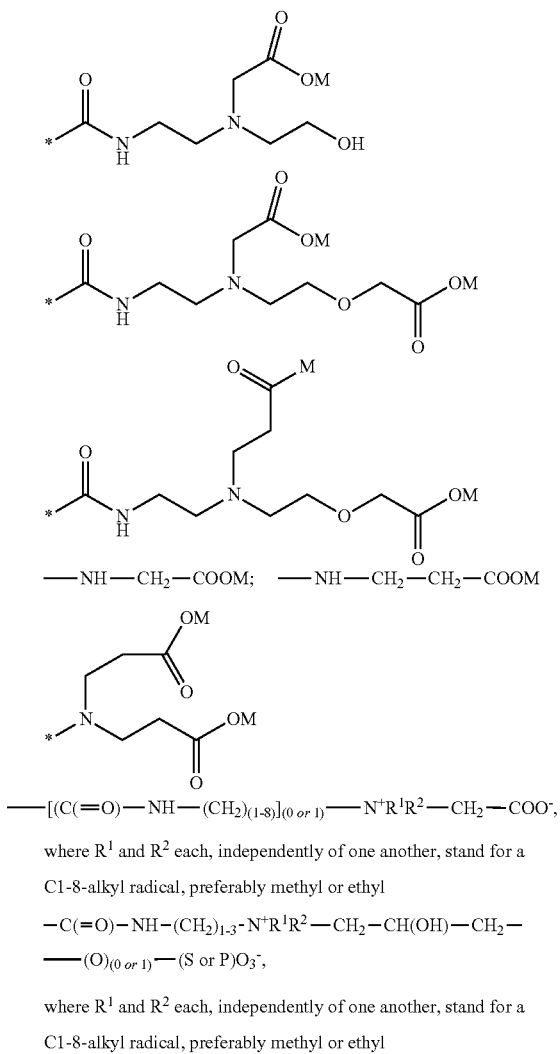

—NH—CH$_2$—COOM;   —NH—CH$_2$—CH$_2$—COOM

—[(C(=O)—NH—(CH$_2$)$_{(1-8)}$]$_{(0\ or\ 1)}$—N$^+$R$^1$R$^2$—CH$_2$—COO$^-$, where R$^1$ and R$^2$ each, independently of one another, stand for a C1-8-alkyl radical, preferably methyl or ethyl

—C(=O)—NH—(CH$_2$)$_{1-3}$-N$^+$R$^1$R$^2$—CH$_2$—CH(OH)—CH$_2$—

——(O)$_{(0\ or\ 1)}$—(S or P)O$_3^-$, where R$^1$ and R$^2$ each, independently of one another, stand for a C1-8-alkyl radical, preferably methyl or ethyl Particularly preferred compounds according to the invention are those which contain, as hydrophilic group X, one of the preferred anionic groups, the preferred non-ionic groups or the preferred zwitterionic groups. Particular preference is given to compounds which contain the groups —SO$_3^-$, —OSO$_3^-$, —COO$^-$, —PO$_3^{2-}$ or OPO$_3^{2-}$, polyethylene glycols or polypropylene glycols, —CH(OH)—CH$_2$—NH-sach, Y—(CH$_2$—CH$_2$—O)$_v$—R$^4$, betaines, or sulfobetaines. Preferred counterions here are H$^+$, Na$^+$, K$^+$ and NH$_4^+$, in particular Na$^+$. Particular preference is given to: —SO$_3$, —COO$^-$, polyethylene glycols or polypropylene glycols, sulfobetaines, the group —CH(OH)—CH$_2$—NH-sach and the group Y—(CH$_2$—CH$_2$—O)$_v$—R$^4$. sach here=various sugars and Y=S, O or NH, preferably O, R$^4$=H or alkyl, preferably H or CH$_3$, and v=1-100, preferably 1-30, in particular also 1-25. Compounds where X=—SO$_3^-$ may also be particularly advantageous.

Advantages of the compounds of the formula (VI') according to the invention may be, in particular:
- a surface activity which is equal or superior to that of conventional hydrocarbon surfactants with respect to efficiency and/or effectiveness,
- biological and/or abiotic degradability of the substances without the formation of persistent perfluorinated degradation products, such as PFOA (perfluorooctanoic acid) or PFOS (perfluorooctanesulfonate),
- can be prepared by simple processes,
- weak foaming action and/or low foam stabilisation,
- good processability in formulations and/or
- storage stability.

The compounds according to the invention can preferably have a particular surface activity. The compounds of the formula (VI') according to the invention, in particular the preferred compounds, may in addition have improved environmental properties, since they do not degrade chemically or biologically to give long-chain PFCAs or PFASs.

The compounds according to the invention can preferably be converted completely into mineralisable/regeneratable compounds by corresponding environmental influences.

The invention likewise relates to the use of compounds of the formula (VI') and compositions comprising compounds of the formula (VI').

The compounds of formula (VI') can preferably be used as surface-active agents, preferably as surfactant, hydrophobicising agent, interface promoter, viscosity reducer, foam stabiliser or emulsifier. The present invention therefore furthermore relates to the use of the compounds according to the invention and the preferred embodiments described above as surface-active agents, for example for improving the flow behaviour and the wetting capacity of coating formulations in particular of the said particularly preferred compounds.

Besides the compounds of the formula (VI'), the mixtures according to the invention may also comprise solvents, additives, assistants and fillers as well as unfluorinated surfactants. Mention may be made by way of example of silicone particles, plasticisers and surface-modified pigments.

Preferred areas of use are, for example, the use of the fluorosurfactants of the formula (VI') according to the invention as additives in preparations for surface coating, such as paints, coatings, protective paints, special coatings in electronic or semiconductor applications (for example photoresists, top antireflective coatings, bottom antireflective coatings) or in optical applications (for example photographic coatings, coatings of optical elements), in agrochemicals, in polishes and waxes, for example for furniture, flooring and automobiles, in particular in floor polishes, in fire-extinguishing compositions, lubricants, in photolithographic processes, in particular in immersion photolithography processes, for example in developer solutions, rinse solutions, immersion oils and/or in the photoresists themselves, especially for the production of printed circuits or in additive preparations for addition to corresponding preparations.

In addition, the compounds which can be used in accordance with the invention as surfactant are suitable for washing and cleaning applications, and for use as additives/surfactants in cosmetic products, such as, for example, hair- and body-care products (for example shampoos, hair rinses and hair conditioners), foam baths, creams or lotions having one or more of the following functions: emulsifiers, wetting agents, foaming agents, glidants, antistatic, agents for increasing the resistance to skin greases.

For use, the fluorosurfactants according to the invention are usually introduced into correspondingly designed preparations. Usual use concentrations are 0.01-1.0% by weight of the surfactants according to the invention, based on the preparation as a whole.

The present invention likewise relates to corresponding compositions comprising the fluorosurfactants according to the invention. Such compositions preferably comprise a vehicle which is suitable for the respective application, and optionally further active substances and/or optionally assistants. Preferred compositions are paint and coating preparations, fire-extinguishing compositions, lubricants, washing and cleaning compositions and deicers or developer solutions, rinse solutions, immersion oils and photo-resists for photolithographic processes, in particular for immersion photolithography processes and in particular for the production of printed circuits, agrochemicals, floor polishes, cosmetic products or hydrophobicising compositions for textile finishing or glass treatment. Preferred compositions here are paint and coating preparations and printing inks.

In addition, the present invention also relates to water-based coating formulations which comprise the fluorosurfactants according to the invention, alone or in a mixture with additives. Coating formulations based on the following synthetic film formers are preferably used: polycondensation resins, such as alkyd resins, saturated/unsaturated polyesters, polyamides/imides, silicone resins; phenolic resins; urea resins and melamine resins, polyaddition resins, such as polyurethanes and epoxy resins, polymerisation resins, such as polyolefins, polyvinyl compounds and polyacrylates.

In addition, the fluorosurfactants according to the invention are also suitable for use in coatings based on natural products and modified natural products. Preference is given to coatings based on oils, polysaccharides, such as starch and cellulose, and also based on natural resins, such as cyclic oligoterpenes, polyterpenes and/or shellac.

The fluorosurfactants according to the invention can be used both in physically curing (thermoplastics) and also in crosslinking (elastomers and thermosets) aqueous coating systems. The fluorosurfactants according to the invention preferably improve the flow and wetting properties of the coating systems.

The present invention relates to all uses mentioned here of fluorosurfactants to be employed in accordance with the invention, in particular of the preferred compounds. The respective use of fluorosurfactants for the said purposes is known to the person skilled in the art, meaning that the use of the fluorosurfactants to be employed in accordance with the invention presents no problems.

The following examples explain the present invention in greater detail without restricting the scope of protection.

EXAMPLES

Abbreviations
PPVE perfluoropropyl vinyl ether
MTBE tert-butyl methyl ether
PPOL-1 2,2,3-trifluoro-3-heptafluoropropyloxypropan-1-ol Determination of the Static Surface Tension The static surface tensions γ of aqueous surfactant solutions having various concentrations c (grams per litre) are determined.
Instrument: Dataphysics tensiometer (model DCAT 11)
Temperature of the measurement solutions: 20°±0.2° C.

Measurement method employed: measurement of the surface tension using the Wilhelmy plate method in accordance with DIN EN 14370.
Plate: platinum, length=19.9 mm In the plate method, the surface or interfacial tension of the surfactant solution is calculated from the force acting on the wetted length of a plate, in accordance with the following formula:

$$\gamma = \frac{F}{L \cdot \cos\theta} = \frac{F}{L}$$

γ=interfacial or surface tension; F=force acting on the balance; L=wetted length (19.9 mm); θ=contact angle. The plate consists of roughened platinum and is thus optimally wetted so that the contact angle θ is close to 0°. The term cos θ therefore reaches approximately the value 1, so that only the measured force and the length of the plate have to be taken into account.

Example 1

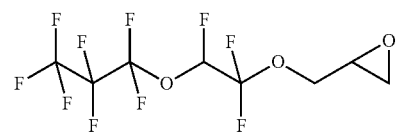

21.78 g of glycidol, 93.86 g of PPVE, 12.19 g of potassium carbonate; 130 ml of dioxane The starting materials are combined in a 300 ml pressure reactor and stirred at 110 C. for 24 h. At the beginning of the reaction, a pressure of 4.5 bar becomes established, this drops to 0.5 bar overnight. Water and MTBE are added to the reaction mixture, and the phases are separated. The aqueous phase is extracted with 2×30 ml of MTBE and the combined organic phase is washed with 40 ml of water and 40 ml of saturated NaCl solution. The extract is dried over sodium sulfate and the solvent is distilled off. Product weight: 90.87 g. The product was distilled in vacuo.

| $T_{bath}$ °C. | $T_{head}$ °C. | p mbar |
|---|---|---|
| 50.3 | 24.1 | 0.80 |

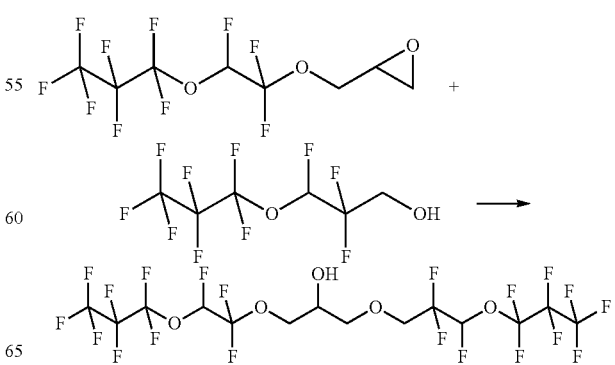

3.40 g of the fluoroepoxide from Example 1, 8.94 g of fluoroalcohol (PPOL-1) and 0.36 g of sodium (elemental)

PPOL-1 is initially introduced in a round-bottomed flask. Elemental sodium is added with cooling. For complete dissolution of the sodium, the reaction mixture is heated gently. The reaction mixture is subsequently called again and the epoxide is added. When the addition is complete, the reaction mixture is stirred at 80° C. for 20 h. MTBE and water are added to the reaction mixture and the phases are separated. The aqueous phase was extracted with 2×30 mL of MTBE. The combined organic phase is washed with in each case 40 ml of water and 40 ml of saturated NaCl solution. The extract is dried over sodium sulfate and the solvent is distilled off. Product weight: 15.04 g.

The product is distilled in vacuo.

| p mbar | $T_{bath}$ °C. | $T_{head}$ °C. |
|---|---|---|
| 0.80 | 105.4 | 78.3 |

Product weight: 4.7 g

Example 2

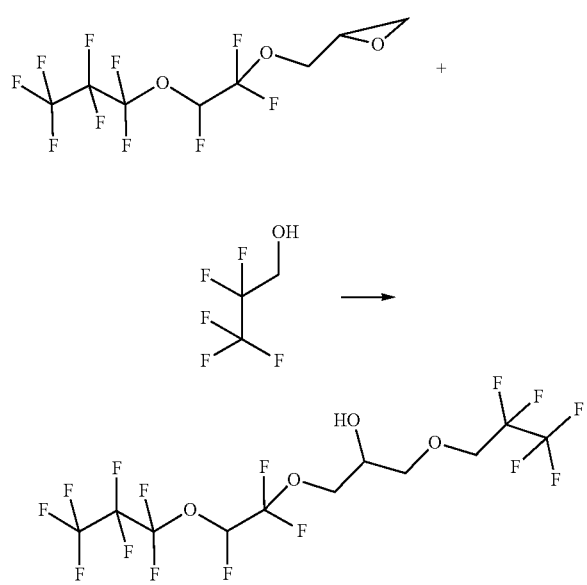

The starting materials are combined in a 50 ml pressure reactor and slowly heated to 130° C. After 20 h, the reaction is terminated and water and MTBE are added to the reaction mixture. The phases are separated and the aqueous phase is extracted with 2×25 mL of MTBE. The combined organic phases is subsequently washed with in each case 30 ml of water and 30 ml of saturated NaCl solution. The extract is dried over sodium sulfate and the solvent is distilled off. The reaction mixture is purified by distillation. Product weight: 6.55 g GC MS shows 82.77% of product and 6.81% of isomer.

Example 3

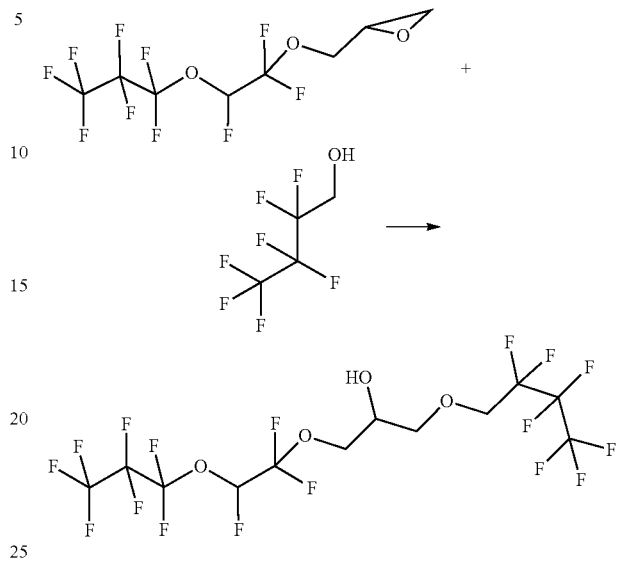

The starting materials are combined in a 50 ml pressure reactor and slowly heated to 130° C. After 20 h, the reaction is terminated and water and MTBE are added to the reaction mixture. The phases are separated and the aqueous phase is extracted with 2×25 mL of MTBE. The combined organic phases is subsequently washed with in each case 30 ml of water and 30 ml of saturated NaCl solution. The extract is dried over sodium sulfate and the solvent is distilled off. GC MS shows: 87.82% of product.

Example 4

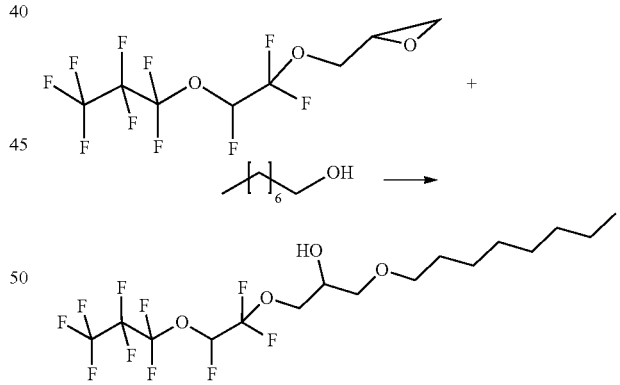

The starting materials are combined in a 50 ml pressure reactor and slowly heated to 130° C. After 20 h, the reaction is terminated and water and MTBE are added to the reaction mixture. The organic phase exhibits an orange coloration. The phases are separated and the aqueous phase is extracted with 2×25 mL of MTBE. The combined organic phases is subsequently washed with in each case 30 ml of water and 30 ml of saturated NaCl solution. The extract is dried over sodium sulfate and the solvent is distilled off. GC MS by means of PCI has a mass peak of 488. This peak corresponds to about 50% of the peak areas. This corresponds to the product plus adducted ammonium.

The invention claimed is:
1. A compound of formula (I')

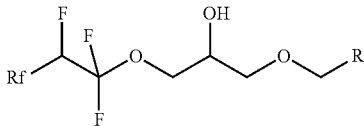 (I')

where
Rf is $CF_3-(CF_2)_a-O_b-(CF_2)_c-O_d-$,
a=1 or 2,
b=1,
c=0,
d=0,
R is a linear or branched alkyl or siloxane group, optionally containing one or more heteroatoms, or a group Rf',
Rf' is a fluorinated, linear or branched alkyl group, optionally containing one or more heteroatoms,
and, if R is a group Rf', Rf and Rf' are different,
or
of formula (VI')

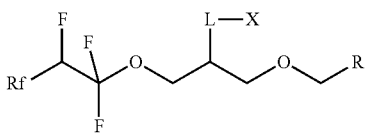 (VI')

where
Rf is a fluorinated, linear or branched alkyl group, optionally containing one or more heteroatoms, R is a linear or branched alkyl or siloxane group, optionally containing one or more heteroatoms,
L is a single bond or a divalent organic group, and
X is a cationic, amphoteric or anionic group.

2. A compound of formula (I')

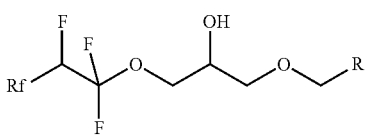 (I')

where
Rf is $CF_3-(CF_2)_a-O_b-(CF_2)_c-O_d-$,
a=1 or 2,
b=1,
c=0,
d=0,
R is a linear or branched alkyl or siloxane group, optionally containing one or more heteroatoms, or a group Rf',
Rf' is a fluorinated, linear or branched alkyl group, optionally containing one or more heteroatoms,
and, if R is a group Rf', Rf and Rf' are different.

3. The compound according to claim 2, wherein Rf is $CF_3-(CF_2)-O-$.

4. The compound according to claim 2, wherein R is a C1-C20 alkyl group.

5. The compound according to claim 2, wherein Rf' is of the following formula

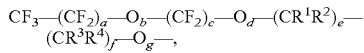

where
$R^1$, $R^2$, $R^3$ and $R^4$, independently of one another, are hydrogen or an alkyl group,
a=0, 1, 2 or 3,
b=0 or 1,
c=0, 1, 2 or 3,
d=0 or 1,
e=0, 1, 2, 3 or 4,
f=0, 1, 2, 3 or 4 and
g=0 or 1.

6. The compound according to claim 2, wherein Rf is $CF_3-(CF_2)_2-O-$.

7. The compound according to claim 1, which is a compound of formula (VI').

8. The compound according to claim 4, wherein Rf is $CF_3-(CF_2)_{0-3}-$ or $CF_3-(CF_2)_{0-3}-O-$.

9. The compound according to claim 7, wherein R is a C1-C20 alkyl group.

10. The compound according to claim 7, which is a compound of formula (VI'), wherein Rf is $CF_3-(CF_2)_{0-3}-O-$.

11. A product selected from the group consisting of paints, coatings, printing inks, protective coatings, special coatings in electronic or optical applications, photoresists, top antireflective coatings or bottom antireflective coatings, developer solutions and wash solutions and photoresists for photolithographic processes, cosmetic products, agrochemicals, floor polishes, photographic coatings and coatings of optical elements, comprising a compound according to claim 7.

12. A composition comprising one or more compounds according to claim 7 and a vehicle which is suitable for an application.

13. The composition according to claim 12, which is selected from the group consisting of paints, coating preparations, fire-extinguishing compositions, lubricants, washing compositions, cleaning compositions, de-icers, developer solutions, wash solutions, photoresists for photolithographic processes, cosmetic products, agrochemicals, floor polishes, hydrophobicising compositions for textile finishing and hydrophobicising compositions for glass treatment.

14. A compound of formula (VI')

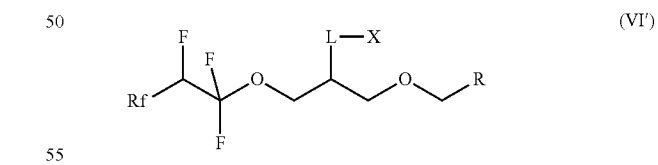 (VI')

wherein
Rf' is of the following formula

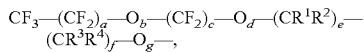

where
$R^1$, $R^2$, $R^3$ and $R^4$, independently of one another, are hydrogen or an alkyl group,
a=0, 1, 2 or 3,
b=0 or 1,
c=0, 1, 2 or 3, d=0 or 1,
e=0, 1, 2, 3 or 4,
f=0, 1, 2, 3 or 4, and
g=0 or 1,
R is a linear or branched alkyl or siloxane group, optionally containing one or more heteroatoms, or a group Rf',
Rf' is a fluorinated, linear or branched alkyl group, optionally containing one or more heteroatoms,
L is a single bond or a divalent organic group, and
X is a cationic, non-ionic, amphoteric or anionic group,
and, if R is a group Rf', Rf and Rf' are different.

15. A compound of formula (VI')

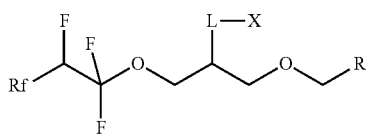
(VI')

wherein
Rf is $CF_3—(CF_2)_{0-3}—$,
R is a linear or branched alkyl or siloxane group, optionally containing one or more heteroatoms, or a group Rf',
Rf' is a fluorinated, linear or branched alkyl group, optionally containing one or more heteroatoms,
L is a single bond or a divalent organic group and
X is a cationic, non-ionic, amphoteric or anionic group
and, if R is a group Rf', Rf and Rf' are different.

16. A method for preparing a compound of formula (VI)

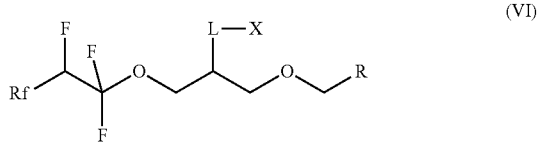
(VI)

where
Rf is a fluorinated, linear or branched alkyl group, optionally containing one or more heteroatoms,
R is a linear or branched alkyl group, optionally containing one or more heteroatoms, or a group Rf',
Rf' is a fluorinated, linear or branched alkyl group, optionally containing one or more heteroatoms,
L is a single bond or a divalent organic group and
X is a cationic, non-ionic, amphoteric or anionic group,
comprising
reacting a compound of formula (I)

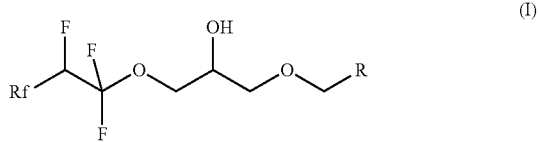
(I)

where
Rf is a fluorinated, linear or branched alkyl group, optionally containing one or more heteroatoms,
R is a linear or branched alkyl or siloxane group, optionally containing one or more heteroatoms, or a group Rf', and
Rf' is a fluorinated, linear or branched alkyl group, optionally containing one or more heteroatoms.

* * * * *